US011547877B2

(12) United States Patent
Kurfurst et al.

(10) Patent No.: US 11,547,877 B2
(45) Date of Patent: Jan. 10, 2023

(54) EXFOLIATING COSMETIC COMPOSITION INCLUDING PIECES OF CANDIED CITRUS FRUIT

(71) Applicant: LVMH RECHERCHE, Saint-Jean de Braye (FR)

(72) Inventors: Chantal Kurfurst, Saint Jean de Braye (FR); Veronique Gerard, Orleans (FR); Dominique Scattarelli, Saint Jean de la Ruelle (FR)

(73) Assignee: LVMH RECHERCHE, Saint-Jean de Braye (FR)

( * ) Notice: Subject to any disclaimer, the term of this patent is extended or adjusted under 35 U.S.C. 154(b) by 475 days.

(21) Appl. No.: 15/750,396

(22) PCT Filed: Jul. 29, 2016

(86) PCT No.: PCT/FR2016/051992
§ 371 (c)(1),
(2) Date: Feb. 5, 2018

(87) PCT Pub. No.: WO2017/021641
PCT Pub. Date: Feb. 9, 2017

(65) Prior Publication Data
US 2018/0214371 A1 Aug. 2, 2018

(30) Foreign Application Priority Data
Aug. 3, 2015 (FR) ...................................... 1557473

(51) Int. Cl.
*A61Q 19/10* (2006.01)
*A61K 8/9789* (2017.01)
*A61K 8/02* (2006.01)

(52) U.S. Cl.
CPC ............ *A61Q 19/10* (2013.01); *A61K 8/0216* (2013.01); *A61K 8/9789* (2017.08); *A61K 2800/28* (2013.01); *A61K 2800/41* (2013.01); *A61K 2800/882* (2013.01)

(58) Field of Classification Search
None
See application file for complete search history.

(56) References Cited

U.S. PATENT DOCUMENTS

| 2,611,708 A | 9/1952 | Owens et al. | |
|---|---|---|---|
| 5,360,824 A * | 11/1994 | Barker | A61K 8/67 424/60 |
| 5,641,814 A * | 6/1997 | Martin | A61K 8/361 514/724 |
| 5,820,915 A * | 10/1998 | Harris | A23L 2/70 426/616 |
| 2004/0022818 A1* | 2/2004 | Cho | A61K 8/9794 424/401 |
| 2004/0091446 A1 | 5/2004 | Massaro et al. | |
| 2009/0068161 A1* | 3/2009 | Gueniche | A61K 31/7048 424/93.46 |

FOREIGN PATENT DOCUMENTS

| CN | 103356455 | 10/2013 | |
|---|---|---|---|
| CN | 103404682 | 11/2013 | |
| FR | 2769178 | 4/1999 | |
| JP | H05339147 | 12/1993 | |
| JP | 2000245382 | 9/2000 | |
| WO | WO-2005030160 A1 * | 4/2005 | ........... A61K 8/9789 |
| WO | 2008078332 | 7/2008 | |

OTHER PUBLICATIONS

International Search Report and Written Opinion issued in International Application No. PCT/FR2016/051992 dated Oct. 18, 2016 (10 pages).
Xiong, L. et al., "Optimization on Ultrasonic Extraction Technology of Total Coumarines in Cortex Fraxini," Journal of Chinese Medicinal Materials, vol. 35, Issue 4, Apr. 2012, pp. 634-637 (with English abstract).
Office Action issued for Chinese Patent Application No. 201680052295. 4, dated Apr. 29, 2020, 40 pages including English translation.
Polin, R. A. et al., "Pediatric Secrets 2E," p. 163, China Ocean Press, Publication Date: Jul. 31, 1999 (with English translation).

\* cited by examiner

*Primary Examiner* — David J Blanchard
*Assistant Examiner* — Sarah J Chickos
(74) *Attorney, Agent, or Firm* — Hamre, Schumann, Mueller & Larson, P.C.

(57) ABSTRACT

The present invention relates to the use of citrus fruit pieces, obtained by controlled osmotic dehydration of said citrus fruit in a sugar syrup, for mechanically exfoliating dead cells from the epidermis of the skin of a person. Said citrus fruit pieces include the peel and/or epicarp of said citrus fruit and have a furocoumarin compound content of less than 50 ppm. The invention also relates to a cosmetic care method intended for skin exfoliation, said method including the steps to involve: applying, onto the skin of a person, citrus fruit pieces obtained by controlled osmotic dehydration of said citrus fruit in a sugar syrup, said citrus fruit pieces including the peel and/or epicarp of said citrus fruit and having a furocoumarin compound content of less than 50 ppm; massaging the skin that is covered by said pieces by rubbing the surface of the skin so as to mechanically exfoliate the dead cells located thereon; and rinsing or wiping the skin in order to remove the candied citrus fruit pieces and the exfoliated dead cells.

13 Claims, No Drawings

EXFOLIATING COSMETIC COMPOSITION INCLUDING PIECES OF CANDIED CITRUS FRUIT

The invention relates to a novel exfoliating cosmetic agent, to cosmetic compositions containing said agent and to a skincare process which uses said agent.

The invention relates more particularly to the use of pieces of fruit having undergone a candying process, as skin exfoliating agent.

PRIOR ART

Various means of exfoliating dead cells from the skin are known.

It is first of all possible to have recourse to mechanical means which use solid particles of small particle size, for instance pumice stone powder, polyethylene powder or nylon powder, polyamide fibers, quartz or rice particles, ground material from husks or stones of fruits, for instance pieces of almond or hazelnut shells, or of peach or apricot stones. Other mechanical means exist, for instance a glove or a material consisting of hair fibers.

It is also possible to act chemically using cosmetic agents which bring about the removal of the dead cells from the horny layer by chemically reducing their cohesion, thus facilitating their detachment (keratolytic action). By way of example, mention may be made of alpha-hydroxy acids (fruit acids) such as glycolic acid, lactic acid, malic acid, or tartaric acid, or beta-hydroxy acids such as salicylic acid.

It is also possible to combine mechanical and chemical means in exfoliating cosmetic compositions.

The desired exfoliation effect is obtained by applying the compositions which comprise the abovementioned exfoliating agents by means of more or less vigorous massaging. The exfoliation of the dead cells from the skin must however be carried out in a controlled manner. This is because all of these means, optionally combined, can cause too strong an abrasion of the horny layer, resulting in the appearance of redness or hypersensitive areas. Exfoliation that is too aggressive can therefore cause a loss, even a partial loss, of the natural barrier and protective function of the superficial layer of the epidermis against aggressive, microbiological or environmental external agents, that can cause the appearance of skin infections or unpleasant sensations.

There is therefore a need for novel exfoliating agents of natural origin which produce a pleasant exfoliating effect on application, and do not risk producing too strong an abrasion of the skin, even in the case of intensive massage.

It has presently been discovered that it is possible to obtain an exfoliating effect on the skin using a material of fruit origin having a flexible texture, contrary to the pieces of fruit husks or stones commonly used. This novel natural exfoliating agent produces an efficient mechanical effect, while remaining particularly pleasant on application, and without risking the generation of irritations.

The inventors have found, completely unexpectedly, that it is possible to obtain a mild exfoliation, friendly to the superficial layer of the epidermis, using pieces of fruits that have been treated by a candying process.

The candying of fruit pieces, and more particularly of pieces at least partly comprising the covering of the fruit, makes it possible to transform the firm texture of a fresh fruit into a supple texture which allows gentle exfoliation of the dead cells from the horny layer by massaging the skin, while providing a pleasant effect.

It is particularly advantageous to thus have available a mechanical exfoliating agent which does not provide any aggressive effect on the skin, in particular too strong an abrasion.

Candying is a fruit preserving process based on the principle of osmosis, which aims to replace the water contained in the fresh fruit with sugar. The fruit is immersed in a sugar-rich syrup in order to cause an exchange between the water of the fruit and the sugar of the syrup. The candied fruit is thus simultaneously enriched in sugar and dehydrated. Candying is a process very widely used in the food industry for fruits of any type which can then be directly consumed or else be used in culinary preparations.

The use of fruits in cosmetic compositions comes up against several difficulties.

Firstly, a high sugar content in an aqueous medium creates conditions conducive to bacterial development, which is detrimental to the stability and the preservation of aqueous cosmetic products.

Secondly, some fruits contain compounds that are harmful to the skin and that prevent them from being used in cosmetic compositions. In the case of citrus fruits, the peel comprises compounds of furocoumarin type which are toxic photosensitive agents. Bergapten, which is photosensitizing, is in particular found in citrus fruit zests. Prolonged contact with these compounds or a plant containing them, followed by exposure to the sun, can cause acute dermatitis. However, it has been noted unexpectedly by the inventors that the candying process applied to citrus fruit peels makes it possible to remove the furocoumarins present in the peel.

The use, in cosmetics, of citrus fruit pieces or of extracts of citrus fruit pieces, more particularly of pieces at least partly comprising peel from said citrus fruit, is therefore made possible by carrying out a candying process. The candying simultaneously removes the water and the offending furocoumarins.

The candying process therefore makes citrus fruit peels usable in cosmetic compositions without risk.

It also makes it possible to improve the stability and the preservation of cosmetic products comprising such citrus fruit peels.

The candying also makes it possible to modify the texture of the fruit pieces. The candying of the citrus fruit peels makes it possible in particular to obtain a softer texture and makes the candied pieces of citrus fruit peel usable as a mechanical exfoliating agent.

The exfoliating effect obtained by these candied pieces of citrus fruits allows gentle exfoliation of the dead cells from the horny layer, which is particularly advantageous for fragile skin or skin that has been made fragile, such as mature skin or skin showing signs of skin dryness or atopic skin.

PURPOSES OF THE INVENTION

The main purpose of the present invention is thus to provide a novel exfoliating cosmetic agent in the form of candied fruit pieces.

An object of the present invention is more particularly to provide a novel exfoliating agent in the form of candied citrus fruit pieces at least partly comprising the peel and/or the epicarp of said citrus fruit.

A subject of the invention is also a cosmetic care product comprising an exfoliating agent in the form of a candied fruit, in particular citrus fruit, piece.

An object of the invention is also to provide a cosmetic care method aimed at gentle exfoliation of the dead cells from the skin by massaging using candied fruit pieces or cosmetic compositions comprising said candied pieces.

DETAILED DESCRIPTION OF THE INVENTION

The invention relates to the use in cosmetics of candied fruit pieces as a mechanical skin exfoliating agent.

The candied fruit pieces can be used alone or in a cosmetic composition comprising at least one cosmetically acceptable excipient, or else in a kit comprising a cosmetic composition.

According to a first variant, the candied fruit pieces are used alone for massaging the skin by means of said fruit pieces.

In a second variant, the candied fruit pieces are impregnated with a cosmetic composition comprising at least one cosmetically acceptable exapient.

According to a third variant, the candied fruit pieces are added as a mechanical exfoliating agent to a cosmetic composition comprising at least one cosmetically acceptable excipient.

In a fourth variant, the candied fruit pieces are presented in a kit in which they are packaged separately from a cosmetic composition included in the kit. In the case where the fruit pieces and the composition are packaged separately, the composition can be manually deposited on the skin and can be spread by means of at least one fruit piece while massaging.

In the second and fourth variants, the candied fruit pieces are used to massage the skin and thus to produce exfoliation thereof. They also serve as applicator supports for the cosmetic composition.

In the case where the fruit pieces are impregnated with composition, it is possible to apply them directly to the skin and to massage the skin.

A first subject of the invention relates to the use of citrus fruit pieces obtained by controlled osmotic dehydration of said citrus fruit in a sugar syrup, for mechanically exfoliating the dead cells from the epidermis of the skin of an individual, said citrus fruit pieces comprising the peel and/or the epicarp of said citrus fruit.

A second subject of the invention is an exfoliating cosmetic care product comprising citrus fruit pieces obtained by controlled osmotic dehydration of said citrus fruit in a sugar syrup, as a mechanical exfoliating agent, said candied pieces comprising the peel and/or the epicarp of said citrus fruit.

The composition of the cosmetic care product of the invention contains a liquid chosen from the group consisting of water, an oil and a mixture of water and oil, and at least one cosmetically acceptable excipient, preferably chosen from surfactants and gelling agents, and even more preferentially a surfactant.

According to a third subject, the invention relates to an exfoliating cosmetic kit comprising
a) a cosmetic composition comprising a liquid chosen from the group consisting of water, an oil and a mixture of water and oil, and at least one excipient chosen from surfactants and gelling agents, and
b) citrus fruit pieces preferably having a size of between 0.1 mm and 5 cm, obtained by controlled osmotic dehydration of said citrus fruit in a sugar syrup,
the composition and the citrus fruit pieces being packaged separately in one and the same packaging.

A fourth subject of the present invention is a skin exfoliating process comprising the steps consisting in applying, to the skin of an individual, citrus fruit pieces preferably having a size of between 0.1 mm and 5 cm, obtained by controlled osmotic dehydration of said citrus fruit in a sugar syrup,
massaging the skin covered with said pieces by rubbing the surface of the skin, so as to mechanically exfoliate the dead cells located thereon,
rinsing or wiping the skin in order to remove the candied citrus fruit pieces and the exfoliated dead cells.

In one embodiment, the fruit used is a citrus fruit Citrus fruits are fruits of plants belonging to the family Rutaeae, in particular of the *Citrus, Fortunella, Microcitrus, Eremocitrus* and *Poncirus* genera, or alternatively hybrid plants obtained by crossing different varieties or species such as *Citrofortunella*.

The citrus fruits can for example be chosen from lemons, clementines, kumquats, bergamots, limes, Tahiti limes, mandarins, oranges, grapefruits, pomelos, tangerines, kaffir limes, yuzus, citrons and calamondin.

The citrus fruit used for the candying consists on the one hand of segments which contain pulp, and on the other hand of a peel, also called pericarp. The peel itself consists of two concentric layers. The superficial layer has a rough and resistant texture, with a vivid color that is often orangey yellow, rich in flavonoids, and is called the epicarp, or zest in cookery. The white spongy internal layer is the mesocarp.

The texture of the epicarp of the fruit is softened by the candying process but retains its roughness and resistance characteristics which make it possible to produce an exfoliating effect without excessive abrasion of the skin while remaining pleasant on application.

For the purposes of the invention, the term "peel" used in the description denotes the epicarp of the citrus fruit or else the epicarp on which the mesocarp and optionally a part of the pulp has been left.

The candied citrus fruit pieces are characterized in that they are at least partly formed from the peel of the citrus fruit.

In one particularly preferred variant, the candied fruit pieces consist of candied citrus fruit peels.

For the implementation of the invention, it is possible to use, without distinction, pieces of a single variety of citrus fruits or of several varieties as a mixture.

Likewise, for a citrus fruit variety, it is possible to use, without distinction, a single candied fraction of the citrus fruit, for example the peel, or several fractions as a mixture.

In the case of mixtures of pieces of various fruits and/or of various fractions of said fruits, at least candied pieces of peel of at least one citrus fruit are used.

As previously explained, the citrus fruit pieces can be exclusively formed from the peel of the citrus fruit, but can also comprise other parts of the citrus fruit, for example a piece of citrus fruit flesh.

According to one preferred variant, the citrus fruit pieces are candied pieces of citrus fruit peel.

Advantageously, the citrus fruit pieces have a size of between 0.1 millimeter and 5 centimeters.

They are advantageously obtained by grinding of peel lamellae of a few centimeters in length, cut from the peel of the citrus fruit. These lamellae can be cut into smaller pieces, before or after candying, depending on the application envisioned.

The candying can thus be carried out on pieces of any size, in the knowledge that it is possible to reduce the size of the pieces by grinding once said pieces have been candied.

The candying comprises several successive steps known to those skilled in the art.

The first series of steps consists in harvesting the fruit, washing it for the purpose of removing any trace of foreign substances (earth, insects, treatment products), optionally bleaching it and cutting it up. The cutting up can be carried out so as to obtain the pieces of desired size just after the osmotic dehydration step, or more coarsely such that the candied fruit pieces of coarse size are ground after dehydration so as to obtain the pieces of desired size.

The bleaching step is a treatment by means of which the fruits or fruit pieces are immersed in water brought to boiling. This treatment makes it possible to break the cell partitions and facilitates penetration of the sugar into the fruit. In the case of citrus fruit peels, the bleaching also makes it possible to remove the bitterness therefrom, by dissolving in water the compounds which are responsible for said bitterness. This step can be repeated several times in order to remove all the bitterness from the peels.

In a second series of steps, the fruits or fruit pieces are brought into contact with at least one sugar solution (syrup) in order to remove the water from the fruits by osmosis.

The sugar syrup can essentially consist of water and at least one sugar. The sugar is chosen from sugars per se, sugar derivatives and polyols. The sugar is for example chosen from sucrose, glucose, invert sugar (equimolar mixture of glucose and fructose obtained by hydrolysis of sucrose), dextrose, sorbitol, fructose and honey.

The syrup can also comprise preservatives, dyes and/or pH correctors.

In the case where the syrup is very concentrated and viscous, it can be slightly heated so as to fluidize it.

The step of removing the water from the fruits by osmosis is preferably carried out until all the water has been removed from the fruit, for example by successively using several syrups. The syrup can be replaced at regular intervals, typically every 24 hours, with a new syrup with a sugar concentration greater than or equal to that of the preceding syrup.

Among the characteristics that can influence the quality of the fruit after candying, mention may be made of the temperature of the baths used for the candying, the method of cutting up the fruits, the contacting time and the number of cycles.

Once the candying has ended, the fruit is separated from the syrup and the excess syrup is allowed to drain off. The candied fruits are cooled where appropriate, and optionally dried.

The candied pieces can be used as they are or else can undergo an additional treatment such as a glazing step in order to obtain a shiny appearance, or else a grinding step in order to once again reduce the size of the candied pieces.

The candied fruit pieces used in the context of the invention have the advantage of being essentially devoid of furocoumarin compounds. For the purposes of the invention, the expression "essentially devoid of furocoumarin compounds" means that the candied fruit pieces contain less than 50 ppm of furocoumarin compounds, preferably less than 20 ppm, more preferably less than 10 ppm, more preferably less than 5 ppm, more preferably less than 4 ppm, preferably less than 3 ppm, more preferably less than 2 ppm. Particularly advantageously, the candied fruit pieces contain less than 1 ppm of furocoumarin compounds.

The candied citrus fruit pieces have for example a Brix degree of between 75 and 85, for example of about 80. The Brix degree of the sugar syrup used in the context of the present invention corresponds to the fraction of sugars present in the syrup, that is to say the percentage of soluble solids. The Brix degree can be measured according to the standard NFV 05109. The apparatus used for the measurement is a refractometer. Depending on the sugar content of the juice, the deviation of daylight by the sample varies and indicates by a colored delimitation the Brix degree. The unit of measurement is the % (percentage of sugar in the syrup).

The candied citrus fruit pieces have for example a pH of between 3 and 4. The pH can be measured according to the standard NFV 1132.

The candied citrus fruit pieces contain sugar syrup, the content of which can vary from 20% to 60% by weight. The content is, for example, 50% when the syrup used is a glucose-fructose syrup.

As previously explained, the invention is also directed toward an exfoliating cosmetic care product comprising candied fruit pieces as a mechanical exfoliating agent. However, the care composition can also comprise one or more other mechanical or chemical exfoliating agents, for instance jojoba wax.

The composition of the invention can in particular comprise one or more cosmetic agents of which the effect is additional to that produced by the candied fruit pieces.

Among these active agents, mention may be made of dermo-protective and lightening D-biotin (vitamin B7), an extract of *Ascophyllum nodosum* which stimulates the SCCE enzyme involved in desquamation, and an extract of *Enantia chlorantha* bark, which decreases sebum secretion and closes the pores. Among the cosmetic agents, mention may also be made of fruit acids (AHA, BHA, grafted AHAs) which have exfoliating, keratolytic and regenerating properties of fruit acids. AHAs have a deep exfoliating action associated with the synthesis of dermal collagen. They stimulate cell renewal of the skin, reduce the surface epidermis and increase the deep epidermis.

Mention may also be made of WATER AND ZINC GLUCONATE AND MAGNESIUM ASPARTATE AND COPPER GLUCONATE for an energizing effect, *VACCINIUM MYRTILLUS* FRUIT EXTRACT AND *CITRUS MEDICA LIMONUM* EXTRACT AND *SACCHARUM OFFICINARUM* (SUGAR CANE) EXTRACT AND *ACER SACCHARUM* (SUGAR MAPLE) EXTRACT AND *CITRUS AURANTIUM DULCIS* (ORANGE) FRUIT EXTRACT which promotes cell renewal, D-PANTHENOL as calmative and moisturizer, and *CITRUS MEDICA LIMONUM* FRUIT EXTRACT which generates a keratolytic action.

The care compositions of the invention contain water, an oil or a mixture of water and oil and can be in any of the galenical forms normally used for an application to the skin of an individual. These compositions are prepared according to the usual methods.

In the exfoliating cosmetic care product of the invention, the citrus fruit pieces can be impregnated with a cosmetic composition comprising a liquid chosen from the group consisting of water, an oil or a mixture of water and oil, and at least one excipient chosen from surfactants and gelling agents, preferably a surfactant.

Alternatively, the exfoliating cosmetic care product is in the form of a cosmetic composition in which the citrus fruit pieces are uniformly distributed, said composition comprising a liquid chosen from the group consisting of water, an oil or a mixture of water and oil, and at least one excipient chosen from surfactants and gelling agents, preferably a surfactant.

The exfoliating care product is advantageously in the form of a composition having the appearance and/or the texture of a marmalade. It is advantageously a gelled, advantageously aqueous, composition in which the candied pieces are dispersed.

The composition can also be an emulsion, advantageously an oi-in-water or water-in-oil emulsion, which has a texture that is required for an exfoliating application.

The compositions can contain adjuvants that are customary in the cosmetics field, such as fats, emulsifiers, hydrophilic or lipophilic gelling agents, hydrophilic or lipophilic active agents, preservatives, antioxidants, fragrances, fillers, screening agents and colorants.

The compositions are formulated for an application to the skin, and have a particularly desired effect for exfoliating the dead cells at the surface of the skin, while providing a pleasant effect on application.

The compositions can for example be in the form of care creams, care gels or masks.

When the composition is an emulsion or a product containing water and a non-emulsifying oil, the composition comprises a fatty phase comprising at least one oil, and also emulsifiers and coemulsifiers chosen from those conventionally used in the cosmetics field.

Among the oils that can be used in cosmetics, mention may be made of mineral oils such as hydrogenated polyisobutene and liquid petroleum jelly, vegetable oils derived from shea butter, sunflower or else apricot kernels, animal oils, synthetic oils, in particular Purcellin oil, isopropyl myristate and ethylhexyl palmitate, and fluoro oils, for instance perfluoropolyethers. Use may also be made of fatty alcohols, fatty acids, for instance stearic acid, waxes, in particular paraffin wax, carnauba wax or beeswax. Use may also be made of silicone oils and, for example, cydomethicone and dimethicone, silicone waxes, silicone resins and silicone gums.

As emulsifiers, mention may for example be made of glyceryl stearate, polysorbate 60, PPG-3 myristyl ether, silicone emulsifiers such as cetyl dimethicone copolyol and sorbitan mono- or tristearate, PEG-40 stearate, and oxyethylenated sorbitan monostearate (20 OE).

The care composition advantageously comprises at least one aqueous-phase or oily-phase gelling agent.

As hydrophilic gelling agents, mention may be made of carboxylic polymers, acrylic copolymers, polyacrylamides, polysaccharides such as cellulose-based derivatives, alginates, natural gums and days, or cosmetically acceptable salts.

In one preferred implementation, the hydrophilic gelling agent is an alginate. In one preferred implementation, the candied pieces are added to a gelled aqueous composition.

The viscosity of the cosmetic composition can be adjusted so as to keep the candied pieces uniformly dispersed in the composition over time.

According to one variant, the viscosity of the composition can be adjusted in such a way that—when the composition is left to stand—the candied pieces rest at the bottom of the pot in which the composition is packaged, then, at the time of use, after shaking so as to resuspend the candied pieces in the composition, the viscosity is sufficient to maintain the uniformity of the composition for the amount of time taken to remove a sample, and thus to enable the user to remove the sufficient amount of the composition for exfoliating care.

According to one alternative implementation, the candied pieces can be impregnated with a cosmetic composition.

In another implementation, a subject of the invention is a kit in which the fruit piece(s) and the cosmetic composition applied to the skin are packaged separately.

A fifth subject of the invention relates to a method for preparing a cosmetic composition comprising:
 a step of candying a fruit, during which at least the fruit is cut up, the fruit is brought into contact with at least one sugar syrup, and at least the candied fruit pieces are drained,
 an optional step of grinding the candied fruit pieces obtained in the preceding step,
 a step of dispersing the candied pieces in a cosmetic composition.

During the candying step, the fruit is immersed in a sugar-rich syrup so as to bring about an exchange between the water of the fruit and the sugar of the syrup. The candied fruit is thus simultaneously enriched with sugar and dehydrated. The candying step can be carried out several times, by recycling the sugar syrup. The sugar is preferably glucose, fructose or invert sugar (an equimolar mixture of the two). The fruit can be fresh, from storage in brine, or defrosted.

Other purposes, characteristics and advantages of the invention will emerge dearly in the light of the explanatory description which follows, provided with reference to examples of cosmetic compositions using this novel exfoliating agent, given simply by way of illustration.

In the example below, all the percentages are given by weight, the temperature is in degrees Celsius, and the pressure is atmospheric pressure, unless otherwise indicated.

Example 1: Exfoliating Aqueous Gel Containing Pieces of Candled Peel of Citrus Fruit Preparation of the Pieces of Candied Peel of Citrus Fruit A mixture of orange, clementine and lemon peel, in equal proportions, is used.

The peel pieces of coarse size are candied separately in several steps, using syrups consisting of water, fructose and glucose, the sugar concentration of which gradually increases. The syrups also comprise a preservative (sulfurous anhydride) and an acidity corrector (citric acid).

After draining and cooling, the pieces are ground so as to obtain pieces that are at most a few millimeters in size.

The candied peel pieces obtained have a Brix degree of 80 and a pH of 3.5.

Preparation of the Exfoliating Aqueous Gel Containing the Candied Citrus Fruit Pieces An aqueous gel having the following formula was prepared. The amounts are expressed in percentages by weight.

| | |
|---|---|
| Pieces of candied orange and clementine peel | 25.0 |
| Pieces of candied lemon peel | 25.0 |
| Glycerol | 2.0 |
| Sodium alginate | 1.5 |
| Phenoxyethanol | 0.3 |
| Tetrasodium EDTA | 0.2 |
| Tocopheryl acetate | 0.2 |
| Sodium citrate | 0.2 |
| Active agents | qs |
| Water | qs 100.0 |

The weight of peels is 50% by weight relative to the weight of the composition, the remainder consisting of a formula of translucent aqueous gel type. The composition has the appearance of a marmalade in which the candied peel pieces are uniformly dispersed.

Exfoliating Care

Tests were carried out on a panel of 11 volunteer subjects who were selected from women over the age of 18 with no skin disorder.

On the morning of the test, the subjects washed with their usual cleansing product, without subsequently applying a care product.

In order to evaluate the exfoliating effect of the product of the invention, adhesives sold under the reference D'Squama® were used. The principle consisted in removing the dead cells present at the surface of the skin, in sticking an adhesive to the skin, and then in removing it. When the adhesive is detached, it brings with it pieces of the first surface layers of the skin (also called squares, which consist of corneocytes). The adhesive can then be analyzed to quantify the squames that have been removed from the skin.

An adhesive is applied to the skin only once. It is in the form of a thin disk 22 mm in diameter.

For each measurement, an adhesive disk was stuck to an area of skin; the disk was kept in place for 10 seconds using an applicator at 300 gf (2.942 N), then detached from the skin.

An image of the disk was then recorded using a camera, an optical microscope and standardized lighting. Image processing software makes it possible to calculate a coefficient (CAI) which quantifies the number and the distribution of the squames present on the disk that were removed from the surface of the skin.

The CAI coefficient is calculated by software on the basis of three parameters: the gray level of the disk (GL), the percentage of squames occupying the surface of the disk (% Scales) and the percentage of corneocytes occupying the surface of the disk (% Corneo), according to the formula below:

$$CAI = 1.5 \times \frac{[GL - (100 - \% \text{ Scales}) \times 2.0] \times 100}{\% \text{ Scales}} + 100 \times \frac{\% \text{ Corneo}}{\% \text{ Scales}}$$

For each subject, the measurement is reproduced three times with a new disk for a given area and at a given time. The CAI value retained is the average of the three measurements.

On an Area 1, intended to be treated, a first measurement of the CAI is carried out before application of the care product (CAIA1 T0), then a second measurement of the CAI is carried out after the care (CAIA1 T1). The exfoliating care consisted in applying the aqueous gel described above to the area of skin in question (Area 1), using a fingerstall, in leaving the gel on the skin for 10 minutes, then in rinsing it with water.

A first measurement of the CAI (CAIA0 T0) at T0, then a second measurement of the CAI at T1 (CAIA0 T1) were carried out on a reference area, Area 0, adjacent to the Area 1, in the knowledge that no product is applied to this Area 0.

For each subject, the following are therefore calculated:
the CAI on a treated Area 1, before application of the care product on the Area 1 (CAIA1 T0), and after application and rinsing of the care product on the Area 1 (CAIA1 T1),
the CAI on a nontreated Area 0 adjacent to the Area 1 of the skin, at time T0 (CAIA0 T0) and at time T1 (CAIA0 T1).

The exfoliating effect of the care product (denoted VAR) was evaluated by measuring the decrease in the amount of squames removed after application of the care product, that is to say the decrease in the CAIA1 T1 relative to the CAIA1 T0, after correction using data collected on the nontreated area A0, adjacent to the treated area A1.

$$\% \, VAR = 100 \times [(CAIA1\,T1 - CAIA1\,T0) - (CAIA0\,T1 - CAIA0\,T0)]/CAIA0\,T1$$

In this study, VAR is 31% on average for all of the panel. The statistical study of the results confirmed that this result was significant.

In conclusion, the composition of the invention has a significant skin exfoliating effect.

Example 2: Exfoliating Aqueous Gel Containing Pieces of Candied Lemon Peel

Preparation of the Pieces of Candied Lemon Peel

The lemon peel pieces are candied according to the same method as that described in example 1.

The furocoumarin content of the pieces of candied lemon peel is determined, before they are used for the preparation of an exfoliating cosmetic care product.

Quantitative Determination of Furocoumarins by HPLC/UV/Fluorimetry

By HPLC:

Chromatographic Conditions:

Column: C18 Gravity Macherey Nagel, 250 mm×4 mm×5 μm

Mobile phase: A: Water/ACN/THF (85/10/5 v/v)
B: MeOH/ACN/THF (30/65/5 v/v)

| Gradient: | 100% A ---> | 100% A ---> | 75% A ---> | 75% A ---> | 70% A ---> | 15% A ---> | 5% A |
|---|---|---|---|---|---|---|---|
| | 4 min | 13 min | 6 min | 7 min | 5 min | 10 min | |

Flow rate: 1 ml/min

Injection volume: 5 μl

Detection: UV at 310 nm

Fluorimetric: excitation at 310 nm, emission at 490 nm.

Preparation of the Standard Solution (0.08 μg/ml):

10 mg of the following three furocoumarins are placed in a 250 ml volumetric flask:

| | |
|---|---|
| 8-methoxypsoralen | CAS 298-81-7 |
| psoralen | CAS 66-97-7 |
| bergapten | CAS 484-20-8 |

The flask is made up to the volume with acetonitrile. The solution is then diluted to 0.2 ml in 100 ml of acetonitrile.

Preparation of the Sample Solution (80 mg/ml):

Exactly 400 mg of sample are placed in a 5 ml volumetric flask.

The flask is made up to the volume with acetonitrile. The solution is then dispersed with magnetic stirring and with ultrasound.

The solutions are then filtered through 0.45 μm, then injected into the HPLC apparatus.

Results:

The three furocoumarins are detected at a content below 1 ppm.

Preparation of the Exfoliating Aqueous Gel Containing the Pieces of Candied Lemon Peel The pieces of candied lemon peel are then used as they are in an exfoliating aqueous gel as described in example 1.

The invention claimed is:

1. A method for mechanically exfoliating dead cells from the epidermis of the skin of an individual, comprising massaging the skin of the individual to which has been applied citrus fruit pieces obtained by controlled osmotic dehydration of said citrus fruit in a sugar syrup, said controlled osmotic dehydration leading to a furocoumarin compound content in said citrus fruit pieces of less than 50 ppm, and said citrus fruit pieces consisting of the peel and/or the epicarp of said citrus fruit and having a content of sugar syrup varying from 20% to 60% by weight, a size of between 0.1 mm and 5 cm.

2. The method as claimed in claim 1, wherein said citrus fruit pieces have a furocoumarin compound content of less than 20 ppm.

3. The method as claimed in claim 1, wherein said citrus fruit pieces are impregnated with a cosmetic composition comprising a liquid chosen from the group consisting of water, an oil or a mixture of water and oil, and at least one excipient chosen from surfactants and gelling agents.

4. The method as claimed in claim 1, wherein said citrus fruit pieces are in the form of a cosmetic composition in which said citrus fruit pieces are uniformly distributed as an exfoliating agent, said composition comprising a liquid chosen from the group consisting of water, an oil or a mixture of water and oil, and at least one excipient chosen from surfactants and gelling agents.

5. The method as claimed in claim 1, wherein the citrus fruit is chosen from lemons, clementines, kumquats, bergamots, limes, Tahiti limes, mandarins, oranges, grapefruits, pomelos, tangerines, kaffir limes, yuzus, citrons and calamondin.

6. The method according to claim 1, wherein the citrus fruit pieces are applied in a cosmetic composition to cover an area of the skin of the individual, the method further comprising:
    massaging the skin covered with the composition by rubbing the surface of the skin, so as to mechanically exfoliate the dead cells located thereon, and
    rinsing or wiping the skin in order to remove the candied citrus fruit pieces and the exfoliated dead cells.

7. The method as claimed in claim 2, wherein the furocoumarin compound content is less than 10 ppm.

8. The method as claimed in claim 7, wherein the furocoumarin compound content is less than 5 ppm.

9. The method as claimed in claim 8, wherein the furocoumarin compound content is less than 1 ppm.

10. The method as claimed in claim 1, wherein the sugar syrup comprises invert sugar.

11. The method as claimed in claim 4, wherein the excipient comprises alginate.

12. The method as claimed in claim 5, wherein the citrus fruit comprises lemon.

13. The method as claimed in claim 1, wherein said citrus fruit pieces have a Brix degree of between 75 and 85.

* * * * *